United States Patent [19]

van der Jagt

[11] Patent Number: Plant 6,545

[45] Date of Patent: Jan. 17, 1989

[54] CHRYSANTHEMUM NAMED "REPIN"

[75] Inventor: Martinus van der Jagt, Ter Aar, Netherlands

[73] Assignee: Chrysantheum Breeders Association NV, Netherlands Antilles

[21] Appl. No.: 782,101

[22] Filed: Sep. 30, 1986

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Parkhurst & Oliff

[57] ABSTRACT

The present invention is a new and distinct variety of Chrysanthemum having a phlox pink bloom.

3 Drawing Sheets

BACKGROUND OF THE INVENTION

The present invention comprises a new and distinct cultivar of Chrysanthemum plant which is a cross of unknown parents. The invention was discovered by Martinus van der Jagt in June 1979 at Paradÿsweg 88, Ter Aar, Holland. The invention has been asexually reproduced by cuttings at the same location. The new cultivar has been found to retain its distinctive characteristics through successive propagations.

BRIEF DESCRIPTION OF THE DRAWINGS

The present invention of a new and distinct variety of Chrysanthemum is shown in the accompanying drawings, the color being as nearly true a possible with color photographs of this type.

FIG. 1 shows the full bloom of the new cultivar.

FIG. 2 shows the various stages of bloom of the new cultivar.

FIG. 3 shows the foliage and stem of the new cultivar.

DESCRIPTION OF THE INVENTION

This new variety of chrysanthemum is the variety botanical classification *Chrysanthemum morifolium* named "Repin". When grown in the vicinity of, Ter Aar, Holland, it has a response time of approximately 10 weeks. This new variety produces medium to large sized blooms having a 3 week performance.

This new variety of Chrysanthemum has been found to retain its distinctive characteristics throughout successive propagations and may be planted under greenhouse conditions in Holland between weeks 1 and 30.

The following is a description of the plant and characteristics that distinguish it over related known varieties and antecedents:

Bud:
- *Size.*—Medium.
- *Form.*—Flat top.
- *Color.*—Pink pastel mauve, RHS 433.

Botanical classification: *Cyrysanthemum morifolium.*

Bloom:
- *Size.*—Medium.
- *Fully open.*—7–9 cms.
- *Borne.*—Single, sometimes several.
- *Stems.*—Strong.
- *Form.*—Single type.
- *Permanence.*—3 weeks.

Color:
- *Center of flower.*—Citron green, RHS 763/3.
- *Base of petals.*—Phlox pink, near RHS 625/3.
- *Inside of petals.*—Phlox pink, near RHS 625/3.
- *Reverse of petals.*—Phlox pink, near RHS 625/3.
- *Outer petals.*—Phlox pink, near RHS 625/3.
- *Tonality from a distance.*—Phlox pink single. Center remains green-yellow even when the styles appear.
- *Discoloration.*—Not much to pale pink.

Petals:
- *Texture.*—Rough (both upper and underside).
- *Number.*—42–45.
- *Arrangement.*—Much imbricated. Two well filled rows.
- *Persistence.*—Normal.
- *Fragrance.*—Typical Chrysanthemum.

Reproductive organs:
- *Stamens.*—Normal.
- *Pollen.*—Appears in normal quantity.
- *Styles.*—Columnar.
- *Length.*—Medium.
- *Stigmas.*—Medium, yellow.
- *Ovaries.*—Enclosed in calyx.

Plant:
- *Form.*—Herbaceous.
- *Growth.*—Vigorous.
- *Height.*—Tall.
- *Peduncle.*—Strong.

Foliage:
- *Color.*—Dark green.
- *Size.*—Medium to large.
- *Quantity.*—Normal.
- *Shape.*—Pointed.
- *Texture.*—Normal.
- *Ribs and veins.*—Ordinary.
- *Edge.*—Deeply undulated.
- *Leaf underside.*—Smooth.
- *Leaf upperside.*—Smooth.

In the description above color references are made to the Horticultural Colour Chart I & II issued by the British Colour Council in collaboration with The Royal Horticultural Society, Copyright Robert F. Wilson, Vol. I 1938; Vol. II, 1941, printed by Henry Stone & Son LTD, Banbury, England.

I claim:

1. A new and distinctive variety of Chrysanthemum named Repin as described and illustrated in the foregoing specification and accompanying drawings.

* * * * *

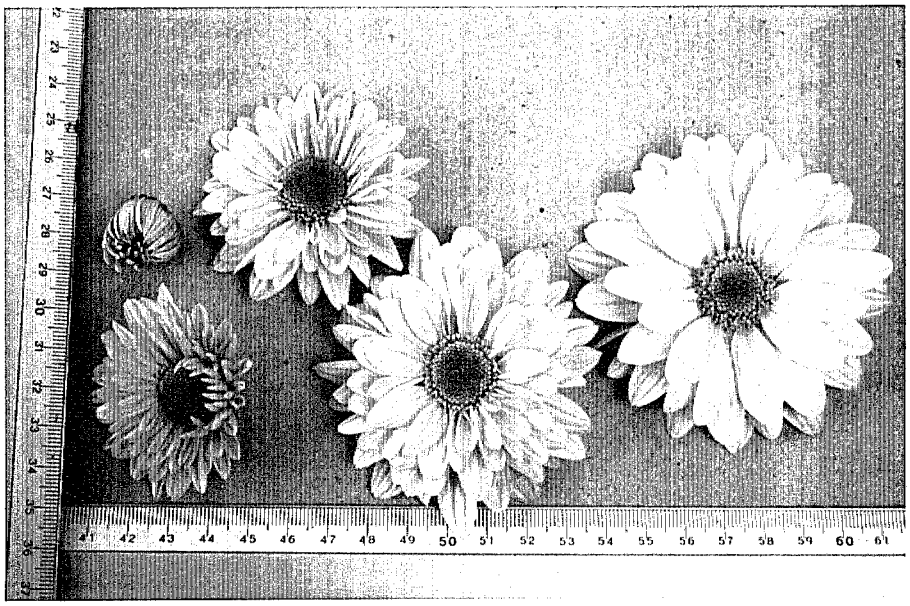

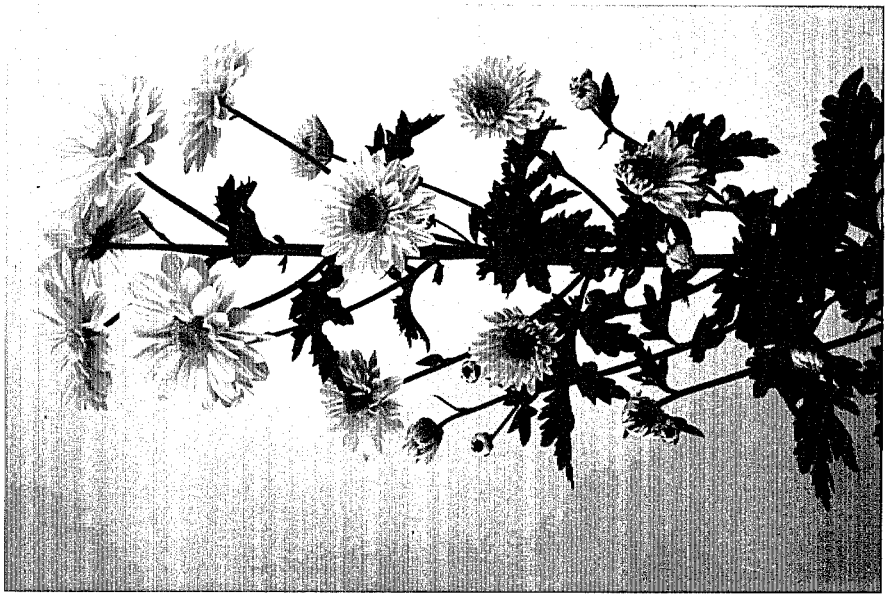
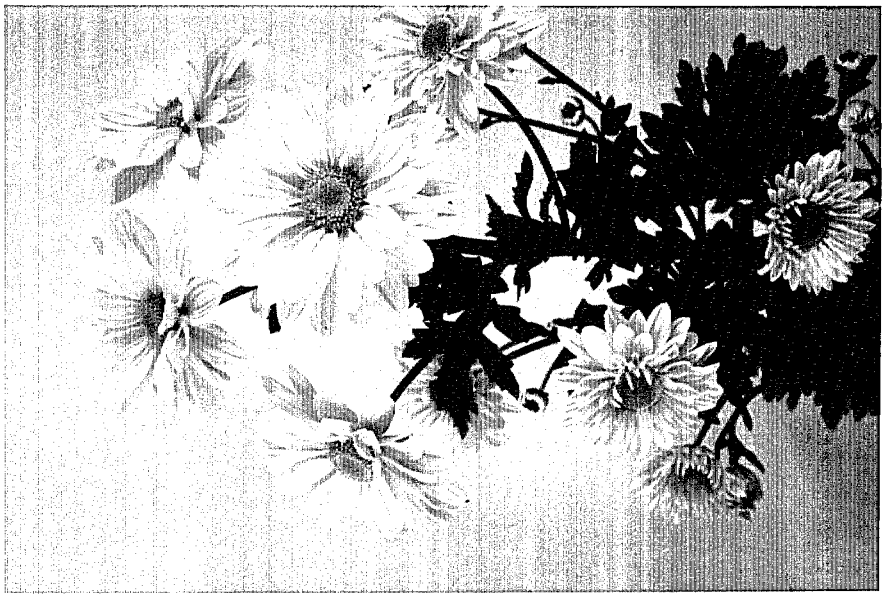

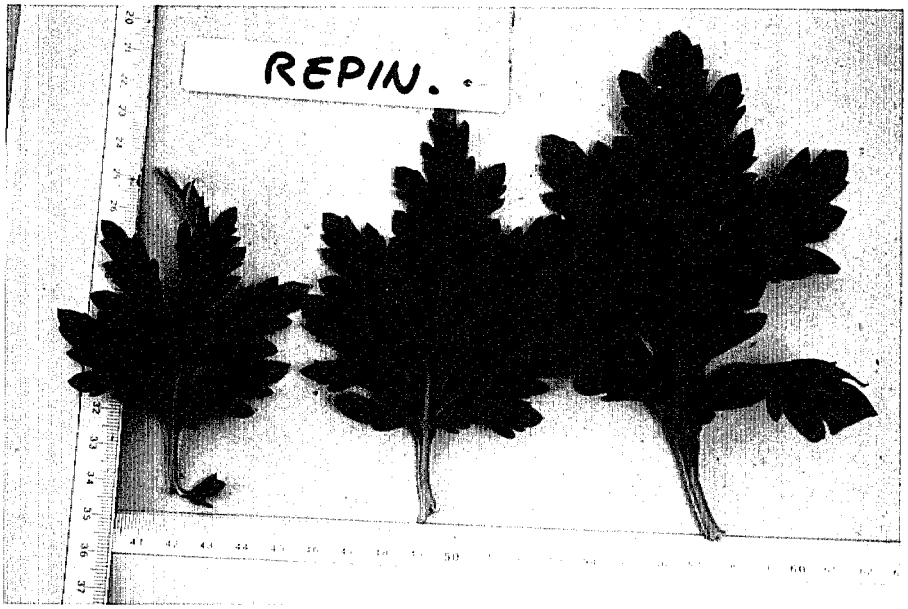
REPIN.